United States Patent [19]

Zinke et al.

[11] 4,290,941

[45] Sep. 22, 1981

[54] STABILIZATION SYSTEMS FROM TRIARYLPHOSPHITES AND PHENOLS

[75] Inventors: Horst Zinke, Ernsthofen; Hans J. Lorenz, Bensheim-Auerbach, both of Fed. Rep. of Germany; Helmut Linhart, Reinach, Switzerland

[73] Assignee: Ciba-Geigy Corporation, Ardsley, N.Y.

[21] Appl. No.: 69,480

[22] Filed: Aug. 24, 1979

Related U.S. Application Data

[63] Continuation of Ser. No. 802,921, Jun. 2, 1977, Pat. No. 4,187,212, which is a continuation of Ser. No. 658,312, Feb. 17, 1976, abandoned.

[30] Foreign Application Priority Data

Feb. 20, 1975 [CH] Switzerland .................. 2155/75
Sep. 19, 1975 [CH] Switzerland .................. 12231/75

[51] Int. Cl.³ ............................................. C08K 5/52
[52] U.S. Cl. .................... 260/45.85 B; 260/45.7 P; 260/45.9 NC; 260/45.95 R; 260/45.95 C; 260/45.95 H
[58] Field of Search ............. 260/45.7 P, 45.95 R, 260/45.85 B, 45.95 B, 45.9 NC, 45.95 C, 45.95 H

[56] References Cited

U.S. PATENT DOCUMENTS

| | | | |
|---|---|---|---|
| 2,915,496 | 12/1959 | Swart et al. | 260/45.7 |
| 2,997,454 | 8/1961 | Leistner et al. | 260/45.8 |
| 3,039,993 | 6/1962 | Friedman | 260/967 |
| 3,080,338 | 3/1963 | Nudenberg et al. | 260/45.7 |
| 3,115,465 | 12/1963 | Orloff et al. | 252/49.9 |
| 3,188,298 | 6/1965 | Williamson et al. | 260/45.85 |
| 3,305,520 | 2/1967 | Fritz et al. | 260/45.7 |
| 3,330,887 | 7/1967 | Conard | 260/920 |
| 3,364,169 | 1/1968 | Oswald et al. | 260/45.95 |
| 3,409,587 | 11/1968 | Mills | 260/45.7 P |
| 3,412,064 | 11/1968 | Brindell | 260/45.85 |
| 3,422,030 | 1/1969 | Riley | 252/400 |
| 3,489,702 | 1/1970 | Abramoff | 260/18 |
| 3,531,483 | 9/1970 | Gilles | 544/221 |
| 3,553,272 | 1/1971 | Riley | 260/624 |
| 3,558,554 | 1/1971 | Kuriyama et al. | 260/45.85 |
| 3,595,936 | 7/1971 | Birenzvige et al. | 260/857 |
| 3,658,743 | 4/1972 | Bevilacqua et al. | 260/23.5 A |
| 3,677,965 | 7/1972 | Dexter et al. | 260/45.9 |
| 3,756,906 | 9/1973 | Leyland et al. | 260/45.7 P |
| 3,803,065 | 4/1974 | Arai | 260/33.4 PQ |
| 3,886,114 | 5/1975 | Beadle | 260/45.7 P |
| 3,960,758 | 6/1976 | Witte et al. | 260/45.95 R |
| 4,013,619 | 3/1977 | Schmidt | 260/45.8 A |

FOREIGN PATENT DOCUMENTS

| | | |
|---|---|---|
| 1065170 | 9/1959 | Fed. Rep. of Germany . |
| 1169662 | 5/1964 | Fed. Rep. of Germany . |
| 1224925 | 9/1966 | Fed. Rep. of Germany . |
| 2300348 | 7/1973 | Fed. Rep. of Germany . |
| 43-15685 | 2/1968 | Japan . |
| 953112 | 3/1964 | United Kingdom . |
| 1150969 | 5/1969 | United Kingdom . |
| 1227719 | 4/1971 | United Kingdom . |
| 1345563 | 1/1974 | United Kingdom . |

Primary Examiner—V. P. Hoke
Attorney, Agent, or Firm—Harry Falber

[57] ABSTRACT

Stabilization system consisting of a triarylphosphite of the general formula

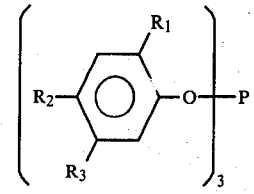

wherein
$R_1$ represents tert.-butyl, 1,1-dimethylpropyl, cyclohexyl or phenyl, and one of
$R_2$ and $R_3$ is hydrogen and the other is hydrogen, methyl, tert.-butyl, 1,1-dimethylpropyl, cyclohexyl or phenyl, and a phenolic antioxidant, for stabilizing polyolefins.

12 Claims, No Drawings

STABILIZATION SYSTEMS FROM TRIARYLPHOSPHITES AND PHENOLS

This is a Continuation of application Ser. No. 802,921 filed on June 2, 1977, now U.S. Pat. No. 4,187,212, which in turn is a continuation of application Ser. No. 658,312, filed Feb. 17, 1976, now abandoned.

The present invention relates to the use of stabilisation systems from triarylphosphites and phenols for stabilising polyolefins against thermooxidative deterioration, as well as to the polyolefins stabilised therewith.

The use of tri-esters of phosphorous acid as stabilisers in polyolefins is known. Furthermore, in J. Voigt, "The Stabilisation of Plastics against Light and Heat", 1st Edition, Springerverlag [Springer publishing house] 1966, page 323, the combination of phosphorous acid esters with other antioxidants is put forward as being their preferred mode of application.

In particular, there is known from U.S. 3,558,554 the use of the three-component combination of "phosphite containing aryl groups"—"phenolic compounds"—"-thiodialiphatic esters" in polyolefins.

Among the "phosphites containing aryl groups" there are many variably substituted (unsymmetrical) phosphites, i.e. those which undergo intermolecular transesterification reactions, which are liquid and which readily hydrolyse, which results in poor storage stability and in an inadequate attainable effectiveness. Moreover, with the addition of thiodialiphatic esters under the processing conditions, there is frequently observed discolouration.

It is clear from GB Pat. No. 1,078,772 that the mixture of aryl-containing phosphites with o-substituted phenols in polyolefins exhibits a particularly good stabilising effect. The high degree of effectiveness is attributed to the o-substituent in the phenol component.

In addition, there is described in U.S. Pat. No. 3,533,989 the special two-component combination of 2,6-ditert.butyl-4-methylphenol with Polygard, (tris-p-nonyl-phenyl phosphites), as a stabiliser for polyolefins. In the same patent specification there is shown the use of tris-(2-tert.butyl-4-methylphenyl)-phosphite, optionally in combination with Polygard. Both combinations contain Polygard, which, as in the case of the above mentioned phosphites, is an oily liquid having the described disadvantages.

It has now been found that, surprisingly, a limited class of symmetrical triarylphosphites of the general formula I

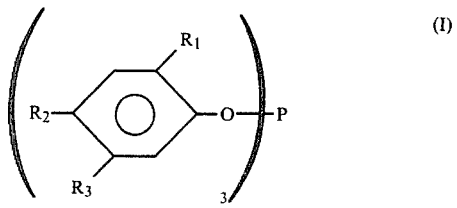

(I)

wherein $R_1$ represents tert.-butyl, 1,1-dimethylpropyl, cyclohexyl or phenyl, and one of $R_2$ and $R_3$ is hydrogen and the other is hydrogen, methyl, tert.-butyl, 1,1-dimethylpropyl, cycohexyl or phenyl, display, in combination with phenolic antioxidants, a particular degree of effectiveness in polyolefins against degradation reactions and cross-linking reactions, such as those normally occurring in the processing of polyolefins.

This particular degree of effectiveness is reflected especially in the excellent absence of discolouration in the resulting polymers, a result which constitutes an advance compared with the results obtained in the case of the prior-art three-component combination described in U.S. Pat. No. 3,558,554. Furthermore, the degree of effectiveness obtained is better than that obtained with the combinations with unsymmetrical phosphites as described in U.S. Pat. No. 3,558,554, or with the combinations with tris-p-nonyl-phenyl phosphite as described in U.S. Pat. No. 3,533,989.

The compounds of the formula I can be used—together with one or more of the phenolic compounds—either singly or in combination with each other. The phosphites usable according to the invention are in most cases crystallised solids, which, compared with the wide range of phosphites known hitherto, are particularly stable also against hydrolysis.

The symbols in the formula I preferably have the following meanings:
$R_1$ represents tert.-butyl or 1,1-dimethylpropyl, and one of
$R_2$ and $R_3$ represents hydrogen, and the other represents hydrogen, methyl, tert.-butyl or 1,1-dimethylpropyl.

A particularly preferred embodiment is one wherein
$R_1$ represents tert.-butyl, and one of
$R_2$ and $R_3$ represents hydrogen, and the other represents hydrogen, methyl or tert.-butyl.

Compounds of the formula I that are especially suitable are, for example:
tris-(2,5-ditert.-butylphenyl)-phosphite,
tris-(2-tert.-butylphenyl)-phosphite,
tris-(2-phenylphenyl)-phosphite,
tris-[2-(1,1-dimethylpropyl)-phenyl]-phosphite,
tris-[2,4-di-(1,1-dimethylpropyl)-phenyl]-phosphite,
tris-(2-cyclohexylphenyl)-phosphite, and
tris-(2-tert.-butyl-4-phenylphenyl)-phosphite;
or, in particular:
tris-(2,4-ditert.-butylphenyl)-phosphite.

The following are be mentioned as examples of phenolic compounds:
1. Single 2,6-dialkylphenols, such as
2,6-di-tert.-butyl-4-methylphenol, 2,6-di-tert.-butyl-4-methoxymethylphenol or 2,6-di-tert.-butyl-4-methoxyphenol.
2. Bisphenols, such as
2,2'-methylene-bis-(6-tert.-butyl-4-methylphenol), 2,2'-methylene-bis-(6-tert.-butyl-4-ethylphenol), 2,2'-methylene-bis-[4-methyl-6-(α-methylcyclohexyl)-phenol], 1,1-bis-(5-tert.-butyl-4-hydroxy-2-methylphenyl)-butane, 2,2-bis-(5-tert.-butyl-4-hydroxy-2-methylphenyl)-butane, 2,2-bis-(3,5-di-tert.butyl-4-hydroxyphenyl)-propane, 1,1,3-tris-(5-tert.butyl-4-hydroxy-2-methylphenyl)-butane, 2,2-bis-(5-tert.-butyl-4-hydroxy-2-methylphenyl)-4-n-dodecylmercapto-butane, 1,1,5,5-tetra-(5-tert.-butyl-4-hydroxy-2-methylpheny)-pentane, ethylene glycol-bis-[3,3-bis-(3'-tert.-butyl-4'-hydroxyphenyl)-butyrate], 1,1-bis-(3,5-dimethyl-2-hydroxyphenyl)-3-(n-dodecylthio)-butane, or 4,4'-thio-bis-(6-tert.-butyl-3-methylphenol).

3. Hydroxybenzyl aromates, such as
1,3,5-tri-(3,5-di-tert.-butyl-4-hydroxybenzyl)-2,4,6-trimethylbenzene, 2,2-bis-(3,5-di-tert.-butyl-4-hydroxybenzyl)-malonic acid-dioctadecyl ester, 1,3,5-tris-(3,5-di-tert.-butyl-4-hydroxybenzyl)-isocyanurate, or 3,5-di-tert.-butyl-4-hydroxybenzyl-phosphonic acid-diethyl ester.

4. Amides of β-(3,5-di-tert.-butyl-4-hydroxyphenyl)-propionic acid, such as 1,3,5-tris-(3,5-di-tert.-butyl-4-hydroxyphenyl-propionyl-hexahydro-s-triazine, N,N'-di-(3,5-di-tert.butyl-4-hydroxyphenyl-propionyl)-hexamethylenediamine.

5. Esters of β-(3,5-di-tert.butyl-4-hydroxyphenyl)-propionic acid with mono- or polyvalent alcohols, such as with methanol, octadecanol, 1,6-hexanediol, ethylene glycol, thiodiethylene glycol, neopentyl glycol, pentaerythritol, tris-hydroxyethyl-isocyanurate.

6. Spiro compounds, such as diphenolic spiro-diacetals or spiro-diketals, such as 2,4,8,10-tetraoxaspiro-[5,5]-undecane substituted in the 3- and 9-position with phenolic radicals, such as 3,9-bis-(3,5-di-tert.butyl-4-hydroxyphenyl)-2,4,8,10-tetraoxaspiro-[5,5]-undecane, 3,9-bis-[1,1-dimethyl-2-(3,5-ditert.-butyl-4-hydroxyphenyl)-ethyl]-2,4,8,10-tetraoxaspiro-[5,5]-undecane.

Particularly preferred phenolic compounds are:
1,3,5-tri-(3,5-di-tert.-butyl-4-hydroxybenzyl)-2,4,6-trimethylbenzene.
pentaerythritol-tetra[3-(3,5-di-tert.-butyl-4-hydroxyphenyl)-propionate],
β-(3,5-di-tert.-butyl-4-hydroxyphenyl)-propionic acid-n-octadecyl ester,
thiodiethylene glycol-β-[4-hydroxy-3,5-di-tert.-butylphenyl]-propionate,
2,6-di-tert.-butyl-4-methyl-phenol, and
3,9-bis-[1,1-dimethyl-2-(3,5-ditert.-butyl-4-hydroxyphenyl)-ethyl]-2,4,8,10-tetraoxaspiro-[5,5]-undecane.

The compounds of the formula I can be produced by methods known per se, for example by reaction of a phenol of the formula II

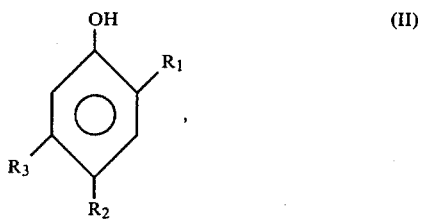

with phosphorus trichloride, without solvent, at 20°–250° C., or in an inert aprotic solvent in the presence of an organic base, or by reaction of a compound of the formula II with triphenylphosphite, preferably without solvent, in the presence of a basic catalyst.

The resulting compounds are purified by recrystallisation in a suitable solvent (solvent mixture).

It is possible with the stabiliser mixture according to the invention to stabilise, for example, the following polyolefins:

1. polymers that are derived from singly unsaturated hydrocarbons, such as polyolefins, e.g. polyethylene of low and high density, can can optionally be crosslinked, polypropylene, polyisobutylene, polymethylbutene-1 and polymethylphentene-1;

2. mixtures of the homopolymers mentioned under 1., such as mixtures of polypropylene and polyethylene, polypropylene and polybutene-1, polypropylene and polyisobutylene;

3. copolymers of the monomers on which the homopolymers mentioned under 1. are based, such as ethylene/propylene copolymers, propylene/butene-1 copolymers, propylene/isobutylene copolymers, ethylene/butene-1 copolymers, as well as terpolymers of ethylene and propylene with a diene, such as hexadiene, di-cyclopentadiene or ethylidenenorbornene.

The stabiliser mixture according to the invention is incorporated at a concentration of 0.005% to 5%, preferably 0.01 to 1%, particularly preferably 0.05 to 0.5%, calculated on the material to be stabilised. The triarylphosphite and the phenolic antioxidant are incorporated in the ratio of 10:1 to 1:5, preferably 5:1 to 1:2, particularly 3:1 to 1:1. Incorporation can be effected by various methods, for example by dry mixing of the polymer with at least one of the compounds of the invention and a phenolic antioxidant, and subsequent processing in a kneading machine, mixing rolls or extruder. The additives mentioned can be applied also in the form of a solution or dispersion to the polymer, with the solvent being subsequently evaporated off.

The following may be mentioned as examples of further additives that can be used together with the combination according to the invention:

1. Aminoaryl derivatives, e.g.
phenyl-1-naphthylamine, phenyl-2-naphthylamine, N,N'-diphenyl-p-phenylenediamine, N,N'-di-2-naphthyl-p-phenylenediamine, N,N'-di-2-naphthyl-p-phenylenediamine, N,N'-di-sec.-butyl-p-phenylenediamine, 6-ethoxy-2,2,4-trimethyl-1,2-dihydroquinoline, 6-dodecyl-2,2,4-trimethyl-1,2-dihydroquinoline, mono- and dioctyliminodibenzyl, polymerised 2,2,4-trimethyl-1,2-dihydroquinoline. Octylated diphenylamine, nonylated diphenylamine, N-phenyl-N'-cyclohexyl-p-phenylenediamine, N-phenyl-N'-isopropyl-p-phenylenediamine, N,N'-di-sec.octyl-p-phenylenediamine, N-phenyl-N'-sec.-octyl-p-phenylenediamine, N,N'-di-(1,4-dimethylpentyl)-p-phenylenediamine, N,N'-dimethyl-N,N'-di-(sec.-octyl)-p-phenylenediamine, 2,6-dimethyl-4-methoxyaniline, 4-ethoxy-N-sec.-butylaniline, diphenylaminecetone condensation product, aldol-1-naphthylamine and phenothiazine.

With the use of this group, discolouration effects have to be taken into account.

2. UV-Absorbers and light-stabilising agents 2.1. 2-(2'-Hydroxyphenyl)-benzotriazoles, e.g. the 5'-methyl, 3',5'-di-tert.-butyl-, 5'-tert.-butyl-, 5'-(1,1,3,3-tetramethylbutyl)-, 5-chloro-3',5'-di-tert.-butyl-, 5-chloro-3'-tert.-butyl-5'-methyl-, 3'-sec.-butyl-5'-tert.-butyl-, 3'-α-methylbenzyl-5'-methyl-, 3'-α-methylbenzyl-5'-methyl-5-chloro-, 4'-hydroxy-, 4'-methoxy-, 4'-octoxy-, 3',5'-di-tert.-amyl-, 3'-methyl-5'-carbomethoxyethyl- and 5-chloro-3',5'-di-tert.-amyl-derivative.

2.2. 2,4-bis-(2'-Hydroxyphenyl)-6-alkyl-s-triazines, e.g. the 6-ethyl-, 6-heptadecyl- or 6-undecyl-derivative.

2.3. 2-Hydroxybenzophenones, e.g. the 4-hydroxy-, 4-methoxy-, 4-octoxy-, 4-decyloxy-, 4-dodecyloxy-, 4-benzyloxy-, 4,2',4'-trihydroxy- or 2'-hydroxy-4,4'-dimethoxy-derivative.

2.4. 1,3-bis-(2'-Hyroxybenzoyl)-benzenes, e.g. 1,3-bis-(2'-hydroxy-4'-hexyloxy-benzoyl)-benzene, 1,3-bis-(2'-hydroxy-4'-octyloxy-benzoyl)-benzene or 1,3-bis-(2'-hydroxy-4'-dodecyloxy-benzoyl)-benzene.

2.5. Esters of optionally substituted benzoic acids, e.g. phenylsalicylate, octylphenylsalicylate, dibenzoylresorcin, bis-(4-tert.-butylbenzoyl)-resorcin, benzoylresorcin, 3,5-di-tert.-butyl-4-hydroxybenzoic acid-2,4-di-tert.-butylphenyl ester or -octadecyl ester or -2-methyl-4,6-di-tert.-butyl ester.

2.6. Acrylates, e.g.
α-cyano-β,β-diphenylacrylic acid-ethyl ester or -isooctyl ester, α-carbomethoxy-cinnamic acid methyl ester, α-cyano-β-methyl-p-methoxy-cinnamic acid methyl ester or -butyl ester or N-(β-carbomethoxyvinyl)-2-methyl-indoline.

2.7. Nickel compounds, e.g.

nickel complexes of 2,2'-thio-bis-[4-(1,1,3,3-tetramethylbutyl)-phenol], such as the 1:1- or 1:2-complex, optionally with additional ligands such as n-butylamine, triethanolamine or N-cyclohexyl-di-ethanolamine, nickel complexes of bis-[2-hydroxy-4-(1,1,3,3-tetramethylbutyl)-phenyl]-sulphone, such as the 2:1-complex, optionally with additional ligands such as 2-ethylcapronic acid, nickeldibutyldithiocarbamate, nickel salts of 4-hydroxy-3,5-di-tert.-butylbenzyl-phosphonic acid-monoalkyl esters, such as of methyl, ethyl or butyl esters, nickel complexes of ketoximes, such as of 2-hydroxy-4-methyl-phenyl-undecylketonoxime, nickel-3,5-di-tert.-butyl-4-hydroxybenzoate or nickel-isopropylxanthogenate.

2.8. Sterically hindered amines, e.g.

4-benzoyl-2,2,6,6-tetramethylpiperidine, 4-stearoyloxy-2,2,6,6-tetramethylpiperidine, bis-(2,2,6,6-tetramethylpiperidyl)-sebacate or 3-n-octyl-7,7,9,9-tetramethyl-1,3,8-triaza-spiro[4,5]decane-2,4-dione.

2.9. Oxalic acid diamides, e.g. 4,4'-di-octyloxy-oxanilide, 2,2'-di-octyloxy-5,5'-di-tert.-butyl-oxanilide, 2,2'-di-dodecyloxy-5,5'-di-tert.-butyl-oxanilide, 2-ethoxy-2'-ethyl-oxanilide, N,N'-bis-(3-dimethylaminopropyl)-oxalamide, 2-ethoxy-5-tert.-butyl-2'-ethyloxanilide and the mixture thereof with 2-ethoxy-2'-ethyl-5,4'-di-tert.-butyl-oxanilide, or mixtures of ortho- and para-methoxy- as well as of o- and p-ethoxy-disubstituted oxanilides.

3. Metal deactivators, e.g.

oxanilide, isophthalic acid dihydrazide, sebacic acid-bis-phenylhydrazide, bis-benzylidene-oxalic acid dihydrazide, N,N'-diacetal-adipic acid dihydrazide, N,N'-bis-salicyloyloxalic acid dihydrazide, N,N'-bis-salicyloylhydrazine, N,N'-bis-(3,5-di-tert.-butyl-4-hydroxyphenylpropionyl)-hydrazine, N-salicyloyl-N'-salicylalhydrazine, 3-salicyloylamino-1,2,4-triazole or N,N'-bis-salicyloyl-thiopropionic acid dihydrazide.

4. Basic co-stabilisers, e.g.

alkali metal salts and alkaline-earth metal salts of higher fatty acids, for example Ca-stearate, Zn-stearate, Mg-behenate, Na-ricinoleate or K-palmitate.

5. Nucleation agents, e.g.

4-tert.-butylbenzoic acid, adipic acid or diphenylacetic acid.

6. Other additives, e.g.

lubricants, e.g. particularly preferred: stearyl alcohol, fillers, carbon black, asbestos, kaolin, talcum, glass fibres, pigments, optical brighteners, flameproofing agents and antistatic agents.

The invention is further illustrated in the following Examples. Percentages (%) denote therein percent by weight, calculated on the material to be stabilised.

EXAMPLE I 100 parts of unstablised polyethylene of high density having a molecular weight of about 500,000 "Lupolen 5260 Z" in powder form from BASF) are in each case mixed dry with 0.05 part of pentaerythritol-tetra-[3-(3,5-di-tert.-butyl-4-hydroxyphenyl)-propionate] and 0.1 part of a stabiliser of the following Table 1 or 2. The mixtures are kneaded in a Brabender plastograph at 220° C. and at 50 r.p.m. for 20 minutes. During this time, the resistance to kneading is continuously recorded as a torsional moment. Owing to cross-linking of the polymer, there occurs during the kneading period, after an initial constant stage, a rapid increase of the torsional moment. The effectiveness of the stabilisers is reflected in a lengthening of the time of constant torsional moment.

The mixtures are subsequently removed from the plastograph and pressed out in a platen press at 260° platen temperature to sheets 1 mm thick, the appearance of which is visually assessed with respect to colour. For the assessment of discolouration in Tables 1 and 2, there is used an empirical colour scale wherein 5 denotes colourlessness, 4 a just perceptible discolouration, and 3, 2, 1 and <1 denote a successively more severe discolouration.

TABLE 1

Effectiveness of the stabiliser combinations of the invention

| Phosphite stabiliser | Time in minutes until change of torsional moment | Discolouration assessment of the sheet specimens |
|---|---|---|
| none | 3½ | 5 |
| tris-(2,4-di-tert.-butyl-phenyl)-phosphite | 10 | 4-5 |
| tris-(2-tert.-butyl-4-methylphenyl)-phosphite | 10½ | 4 |
| tris-(2-tert.-butyl-5-methylphenyl)-phosphite | 9 | 4 |

TABLE 2

Effectiveness of the unsymmetrical triphosphites described in U.S. Pat. No. 3,558,554

| Phosphite stabiliser | Time in minutes until change of torsional moment | Discolouration assessment of the sheet specimens |
|---|---|---|
| none | 3½ | 5 |
| di-n-butyl-(2-tert.-butyl-4-methylphenyl)-phosphite | 4 | 4 |
| di-phenyl-(2-tert.-butyl-4-methylphenyl)-phosphite | 4½ | 4-5 |
| di-n-butyl-(2,6-di-tert.-butyl-4-methylphenyl)-phosphite | 6½ | 2 (speckled inhomogeneous) |

From the results shown in Tables 1 and 2 it is clear that, compared with the comparative products given in Table 2, the triarylphosphites of the formula I in Table I display in polyolefins a very high degree of effectiveness. In particular the concomitant use of dilaurylthiodipropionate leads to a plastics material having poor colour properties.

EXAMPLE II 100 parts of unstabilised polyethylene of high density having a molecular weight of about 500,000 ("Lupolen 5260 Z" in powder form from BASF) are in each case mixed dry with 0.1 part of dilaurylthiodipropionate and with the stabilisers shown in the following Table 3. The mixtures are kneaded in a Brabender plastograph at 220° C. and 50 r.p.m. for 20 minutes. During this time, the resistance to kneading is continuously recorded as a torsional moment. As a consequence of cross-linking of the polymer there occurs in the course of kneading, after an initial constant condition, a rapid rise of the torsional moment. The effectiveness of the stabilisers is expressed in a lengthening of the time of constant torsional moment. The mixtures are subsequently removed from the plastograph and pressed out in a platen press at 260° C. platen temperature into the form of 1 mm thick sheets, the appearance of which is visually assessed with respect to colour. For the assessment of discolouration in Table 3, there is used an empirical colour scale wherein 5 denotes colourlessness, 4 denotes a slight discolouration just perceptible, and 3, 2, 1 and <1 denote a successively more severe discolouration.

TABLE 3

| Parts of stabiliser | Time in minutes until change of torsional moment | Discolouration assessment of the sheet specimens |
| --- | --- | --- |
| 0.05 part of pentaerythritol-tetra-3-(3,5-di-tert.-butyl-4-hydroxyphenyl)-propionate | 2½ | 1 |
| 0.05 part of pentaerythritol-tetra-3-(3,5-di-tert.-butyl-4-hydroxyphenyl)-propionate + 0.1 part of tris-(2-tert.-butyl-4-methylphenyl)-phosphite | 5 | <1 |
| 0.05 part of pentaerythritol-tetra-3-(3,5-ditert.-butyl-4-hydroxyphenyl)-propionate + 0.1 part of tris-(2,4-ditert.-butylphenyl)-phosphite | 6 | <1 |
| 0.05 part of 1,1,3-tris-(5-tert.-butyl-4-hydroxy-2-methylphenyl)-butane | 5½ | <1 |
| 0.05 part of 1,1,3-tris-(5-tert.-butyl-4-hydroxy-2-methylphenyl)-butane + 0.1 part of tris-(2-tert.-butyl-4-methylphenyl)-phosphite | 9 | <1 |
| 0.05 part of 2,6-di-tert.-butyl-4-methylphenol | 5 | <1 |
| 0.05 part of 2,6-di-tert.-butyl-4-methylphenol + 0.1 part of tris-(2-tert.-butyl-4-methylphenyl)-phosphite | 10½ | <1 |

The results show that, independent of the employed antioxidant, there is obtained with the concomitant use of dilaurylthiodipropionate a plastics material which has poor colour properties and which gives in some cases low times of constant torsional moment.

EXAMPLE III 100 parts of unstabilised polyethylene of high density having a molecular weight of about 500,000 ("Lupolen 5260 Z" in powder form from BASF) are mixed dry with the stabilisers of the following Table 4 in the given concentrations. The mixtures are kneaded in a Brabender plastograph at 220° C. and 50 r.p.m. for 20 minutes. During this time the resistance to kneading is continuously recorded. As a consequence of cross-linking of the polymer, there occurs in the course of the kneading process, after an initial constant condition, a rapid rise in the torsional moment. The effectiveness of the stabilisers is expressed in a lengthening of the time of constant torsional moment.

TABLE 4

| Parts of stabiliser | Time in minutes to change of the torsional moment |
| --- | --- |
| none | 2 |
| 0.15 part of pentaerythritol-tetra-[3-(3,5-di-tert.-butyl-4-hydroxyphenyl)-propionate] | 6 |
| 0.15 part of tris-(2-tert.-butyl-4-methylphenyl)-phosphite | 4 |
| 0.05 part of pentaerythritol-tetra- | |

TABLE 4-continued

| Parts of stabiliser | Time in minutes to change of the torsional moment |
| --- | --- |
| [3-(3,5-di-tert.-butyl-4-hydroxyphenyl)-propionate] + 0.10 part of tris-2-tert.-butyl-4-methylphenyl)-phosphite | 10½ |

It follows from the data that with the same total concentration the combination according to the invention produces a protective effect that is clearly better compared with that obtained with the stabilisers used separately.

EXAMPLE IV 100 parts of unstabilised polyethylene of high density having a molecular weight of about 500,000 ("Lupolen 5260 Z" in powder form from BASF) are in each case mixed dry with 0.1 part of tris-(2-tert.-butyl-4-methylphenyl)-phosphite and 0.05 part of the phenolic antioxidants shown in the following Table 5. The mixtures are kneaded in a Brabender plastograph at 220° and 50 r.p.m. for 20 minutes. During this time, the resistance to kneading is continuously recorded as a torsional moment. As a consequence of cross-linking of the polymer there occurs in the course of kneading, after an initial constant phase, a rapid rise of the torsional moment. The effectiveness of the stabilisers is expressed in a lengthening of the time of constant torsional moment

TABLE 5

| Phenolic antioxidant | Time in minutes to change of the torsional moment |
| --- | --- |
| none | 4 |
| pentaerythritol-tetra-[3-(3,5-di-tert.-butyl-4-hydroxyphenyl)-propionate | 10½ |
| 1,1,3-tris-(5-tert.-butyl-4-hydroxy-2-methylphenyl)-butane | 8 |
| 3-(3,5-di-tert.-butyl-4-hydroxyphenyl)-propionic acid-octadecyl-ester | 7 |
| 1,3,5-tri-(3,5-di-tert.-butyl-4 hydroxybenzyl)-2,4,6-trimethylbenzene | 8 |
| 2,2'-methylene-bis-(6-tert.-butyl-4-methylphenol) | 10 |
| 4,4'-thiobis-(6-tert.-butyl-3-methylphenol) | 11 |

The results show that with a wide selection of phenolic compounds in combination with the triarylphosphites according to the invention there is obtained an excellent stabilisation of polyethylene of high density.

EXAMPLE V 100 parts of unstabilised polyethylene of high density having a molecular weight of about 500,000 ("Lupolen 5260 Z" in powder form from BASF) are mixed dry with the stabilisers given in Table 6 at the given concentrations. The mixtures are kneaded in a Brabender plastograph at 220° C. and 50 r.p.m. for 20 minutes. The resistance to kneading during this time is continuously recorded as a torsional moment. As a consequence of cross-linking of the polymer there occurs in the course of kneading, after an initial constant condition, a rapid increase of the torsional moment. The effectiveness of the stabilisers is expressed in a lengthening of the time of constant torsional moment.

TABLE 6

Effectiveness of the stabiliser combinations according to the invention compared with that of the systems described in U.S. Pat. No. 3,533,989.

| Parts of stabiliser | Time in minutes until change of the torsional moment |
|---|---|
| 0.05 part of 2,6-ditert.-butyl-4-methylphenol + 0.1 part of tris-(2-tert.-butyl-4-methylphenyl)-phosphite | 10 |
| 0.05 part of 2,6-ditert.-butyl-4-methylphenol + 0.1 part of tris-(2,4-ditert.-butylphenyl)-phosphite | 12 |
| 0.05 part of 2,6-ditert.-butyl-4-methylphenol + 0.1 part of Polygard (tris-p-nonylphenyl-phosphite | 5 |
| 0.15 part of tris-(2-tert.-butyl-4-methylphenyl)-phosphite | 4 |

EXAMPLE VI 100 parts of unstabilised polyethylene of high density having a molecular weight of about 500,000 ("Lupolen 5260 Z" in powder form from BASF) are mixed dry with 0.05 part of 3-(3,5-di-tert.-butyl-4-hydroxyphenyl)-propionic acid-octadecyl ester and 0.1 part of tris-(2-tert.-butyl-4-methylphenyl)-phosphite.

250 kg of this mixture is processed in an extrusion-blow apparatus (Type VB 250, VOITH) at 227° C. nozzle temperature into the form of 120-liter barrels (frequency: 10 minutes per shot; 1 shot: 10 kg of material). The barrels have a smooth inner surface and are free of lattice or honey-comb structure. Lattice or honey-comb structure or a rough inner surface are the result of an occurring cross-linking of the material.

EXAMPLE VII 100 parts of polypropylene powder (Propathen HF 20, ICI) are homogeneously mixed with the stabilisers listed in the following Table 7 at the stated concentrations. The mixtures obtained are extruded and granulated five times in succession in a single screw extruder at a maximum of 260° C. (temperature of the discharge zone) and 100 r.p.m..

The melt index of the material is measured after the 1st, 3rd and 5th extrusion. The load is 2160 g at 230° C.; the melt index is given in g/10 min.. The degradation of the material is indicated by an increase of the melt index.

TABLE 7

| Parts of stabiliser | Melt index after given number of extrusions | | |
|---|---|---|---|
| | 1 | 3 | 5 |
| none | 14 | 42 | 76 |
| 0.15 part of pentaerythritol-tetra-[3-(3,5-di-tert.-butyl-4-hydroxyphenyl)-propionate] | 4.8 | 6.5 | 9.0 |
| 0.15 part of tris-(2,4-di-tert.-butylphenyl)-phosphite | 4.0 | 8.0 | 12.3 |
| 0.075 part of pentaerythritol-tetra-[3-(3,5-di-tert.-butyl-4-hydroxyphenyl)-propionate] + 0.075 part of tris-(2,4-di-tert.-butylphenyl)-phosphite | 3.5 | 5.0 | 7.4 |
| 0.05 part of pentaerythritol-tetra-[3-(3,5-di-tert.-butyl-4-hydroxyphenyl)-propionate] + 0.1 part of tris-(2,4-di-tert.-butylphenyl)-phosphite | 3.3 | 4.9 | 6.6 |
| 0.03 part of pentaerythritol-tetra-[3-(3,5-di-tert.-butyl-4-hydroxyphenyl)-propionate + 0.12 part of tris-(2,4-di-tert.-butylphenyl)-phosphite | 3.2 | 4.5 | 6.5 |
| 0.15 part of 3,9-bis-[1,1-dimethyl-2(3,5-di-tert.-butyl-4-hydroxyphenyl)-ethyl]2,4,8,10-tetraoxaspiro-[5,5]undecane | 4.9 | 6.8 | 9.0 |
| 0.05 part of 3,9-bis-[1,1-dimethyl-2(3,5-di-tert.-butyl-4-hydroxyphenyl)-ethyl]2,4,8,10-tetraoxaspiro-[5,5]undecane + 0.1 part of tris-(2,4-di-tert.-butylphenyl)-phosphite | 3.4 | 4.5 | 6.2 |

We claim:

1. A stabilized composition consisting essentially of (a) a polymer that is derived from a singly unsaturated acyclic hydrocarbon, or mixtures or copolymers thereof; and (b) from 0.005 to 5% of a mixture of (1) a triarylphosphite of the general formula

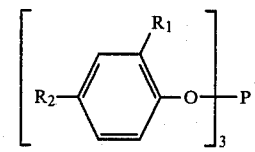

wherein $R_1$ is tert.butyl or 1,1-dimethylpropyl, and $R_2$ is methyl, tert.butyl or 1,1-dimethylpropyl, and (2) a hindered phenolic antioxidant selected from the group consisting of 2,6-di-tert.butyl-4-methylphenol, 2,2'-methylene-bis(6-tert.butyl-4-methylphenol), 2,2'-methylene-bis(6-tert.butyl-4-ethylphenol), 2,2'-methylene-bis(4-methyl-6-α-methylcyclohexyl) phenol, 1,1,3-tris(5-tert.butyl-4-hydroxy-2-methylphenyl) butane, 4,4'-thiobis(6-tert.butyl-3-methylphenol), 3,5-di-tert.butyl-4-hydroxybenzyl-phosphonic acid diethylester, N,N'-di-(3,5-di-tert.butyl-4-hydroxyphenylpropionyl)-hexamethylenediamine, 1,2-bis(3,5-di-tert.butyl-4-hydroxyphenyl-propionyloxy)-ethane, 1,5-bis(3,5-di-tert.butyl-4-hydroxyphenyl-propionyloxy)-2-thiapentane, 1,3-bis(3,5-di-tert.butyl-4-hydroxyphenyl-propionyloxy)-2,2-dimethylpropane and 1,1-bis(5-tert.butyl-4-hydroxy-2-methylphenyl)-butane; the ratio of the phosphite to the antioxidant being from 10:1 to 1:5.

2. The composition of claim 1, wherein said phosphite is tris(2,4-di-tert.butylphenyl)-phosphite.

3. The composition of claim 1, wherein said phosphite is tris(2-tert.butyl-4-methylphenyl)-phosphite.

4. The composition of claims 1, 2 or 3, wherein said phenol is 2,6-di-tert.butyl-4-methylphenol.

5. The composition of claim 1, wherein said polymer is polyethylene or polypropylene.

6. The composition of claim 4, wherein said polymer is polyethylene or polypropylene.

7. A method of stabilizing polymers derived from singly unsaturated, acyclic hydrocarbons or mixtures or copolymers thereof, which comprises incorporating in said polymer from 0.005 to 5% of mixture (b) according to claim 1.

8. The method of claim 7, wherein said phosphite is tris-(2,4-di-tert.butylphenyl)-phosphite.

9. The method of claim 7, wherein said phosphite is tris(2-tert.butyl-4-methylphenyl)-phosphite.

10. The method of claims 7, 8 or 9, wherein said phenol is 2,6-di-tert.butyl-4-methylphenol.

11. The method of claim 7, wherein said polymer is polyethylene or polypropylene.

12. The method of claim 10, wherein said polymer is polyethylene or polypropylene.

* * * * *